United States Patent
Knebel

(10) Patent No.: US 6,878,948 B2
(45) Date of Patent: Apr. 12, 2005

(54) METHOD AND ARRANGEMENT FOR LOCATING SPECIMEN REGIONS

(75) Inventor: Werner Knebel, Kronau (DE)

(73) Assignee: Leica Microsystems Heidelberg GmbH, Mannheim (DE)

(*) Notice: Subject to any disclaimer, the term of this patent is extended or adjusted under 35 U.S.C. 154(b) by 465 days.

(21) Appl. No.: 10/026,221

(22) Filed: Dec. 19, 2001

(65) Prior Publication Data

US 2002/0086433 A1 Jul. 4, 2002

(30) Foreign Application Priority Data

Dec. 30, 2000 (DE) .......................................... 100 65 784

(51) Int. Cl.$^7$ .......................... G01N 33/00; G01N 21/76
(52) U.S. Cl. ................................ 250/461.2; 250/459.1; 435/29
(58) Field of Search .................... 250/461.2, 461.1, 250/459.1; 435/29

(56) References Cited

U.S. PATENT DOCUMENTS

| | | | | |
|---|---|---|---|---|
| 4,972,258 A | | 11/1990 | Wolf et al. .................... 358/93 |
| 5,127,730 A | | 7/1992 | Brelje et al. ................. 356/318 |
| 5,296,703 A | * | 3/1994 | Tsien .......................... 250/235 |
| 5,474,910 A | * | 12/1995 | Alfano ......................... 435/34 |
| 5,936,731 A | * | 8/1999 | Cabib et al. ................. 356/456 |
| 6,020,591 A | * | 2/2000 | Harter et al. ............. 250/458.1 |
| 6,166,385 A | | 12/2000 | Webb et al. .............. 250/458.1 |
| 6,396,053 B1 | | 5/2002 | Yokoi .......................... 250/234 |
| 6,462,771 B1 | | 10/2002 | Kitagawa ..................... 348/79 |
| 6,614,525 B1 | * | 9/2003 | Engelhardt et al. ......... 356/318 |
| 6,662,039 B2 | * | 12/2003 | Yuste et al. ................. 600/431 |

| | | | |
|---|---|---|---|
| 2002/0020819 A1 | * | 2/2002 | Wolleschensky et al. 250/459.1 |
| 2003/0170898 A1 | * | 9/2003 | Gundersen et al. ......... 435/461 |

FOREIGN PATENT DOCUMENTS

| | | |
|---|---|---|
| DE | 4221063 | 6/1984 |
| DE | 3915421 | 11/1990 |
| DE | 4330347 | 3/1995 |
| DE | 19757740 | 7/1999 |
| JP | 10010436 | 1/1998 |
| JP | 2000199855 | 7/2000 |
| JP | 2000275539 | 10/2000 |
| WO | 9507447 | 3/1995 |
| WO | 0068667 | 11/2000 |

OTHER PUBLICATIONS

Koester et al. "Ca2+ Fluorescence Imaging with Pico– and Femtosecond Two–Photon Excitation: Signal and Photodamage"; Oct. 1999 in Biophysical Journal vol. 77 pp. 2226–2236.

Piston et al. "Two–photon–excitation fluorescence imaging of three dimensional calcium–ion activity"; Feb. 1, 1994 in Applied Optics vol. 33 pp. 662–669.

* cited by examiner

Primary Examiner—Albert Gagliardi
(74) Attorney, Agent, or Firm—Davidson, Davidson & Kappel, LLC

(57) ABSTRACT

The invention discloses a method for locating specimen regions of interest in a stimulatable microscopic specimen (13) that comprises the steps of: introducing into a specimen (13) of at least two stimulation-specific stains, illuminating with at least one illuminating light beam (7), initiating a stimulation, detection (4) of the light (16) emerging from the stimulation-specific stains, and identifying (5) of the spatial position of the regions within the specimen (13) from which light of at least two different wavelengths that are emission wavelengths of the stimulation-specific stains is emerging.

15 Claims, 3 Drawing Sheets

METHOD AND ARRANGEMENT FOR LOCATING SPECIMEN REGIONS

CROSS REFERENCE TO RELATED APPLICATIONS

This invention claims priority of the German patent application 100 65 784.2-52 which is incorporated by reference herein.

FIELD OF THE INVENTION

The invention concerns a method for locating specimen regions of interest in a stimulatable microscopic specimen.

The invention further concerns an apparatus for locating specimen regions of interest in a stimulatable microscopic specimen.

BACKGROUND OF THE INVENTION

In the examination of microscopic specimens in which dynamic processes that can be stimulated externally occur, individual regions of the specimen are often of particular interest. The stimulation can refer to initiation, termination, or any other influencing of a process.

In cell biology, the transmission of information from cell to cell is studied. The nerve cells branch among and are in contact with one another. At the contact points, so-called spines that are located on the dendrites of the cells are linked to the synapses of another cell. A method for locating the contact points is based on preparing the nerve cells with a stain, for example a calcium indicator such as "calcium green," that emits a characteristic fluorescent light when illuminated with light of a suitable exciting wavelength. By stimulation with a voltage pulse that is applied to the cell tissue, it is possible to induce the transition to an action potential that propagates from cell to cell. This is associated with an inflow of calcium into the spines that is detectable by way of the calcium indicator. One such method is known from the article "$Ca^{2+}$Fluorescence Imaging with Pico- and Femtosecond Two-Photon Excitation: Signal and Photodamage," Helmut J. Koester et al., Biophysical Journal, Vol. 77, October 1999, 2226–2236.

The known method has the disadvantage that the contact points cannot be reliably and reproducibly localized; the reason is that, because the processes at the contact points take so little time, only a few indicator molecules are excited and therefore only a few characteristic photons are generated, yielding a very poor signal-to-noise ratio. Locating the contact points is therefore a very laborious process, and requires a great deal of experience and intuition on the part of the user.

SUMMARY OF THE INVENTION

It is therefore the object of the invention to describe a method for locating specimen regions of interest in a stimulatable microscopic specimen that possesses increased reliability, reproducibility, and accuracy as compared to known methods, and moreover is faster.

The aforesaid object is achieved by a method which comprises the following steps:
introducing into the specimen of at least two stimulation-specific stains that emit light of different wavelengths;
illuminating at least a portion of the specimen with at least one illuminating light beam;
initiating a stimulation;
detecting the light emerging from the stimulation-specific stains; and
identifying the spatial position of the regions within the portion of the specimen from which light of at least two different wavelengths that are emission wavelengths of the stimulation-specific stains is emerging.

A further object of the invention is to describe an apparatus for locating specimen regions of interest in a stimulatable microscopic specimen.

The object is achieved by an apparatus comrising: a means for illuminating at least a portion of the specimen with at least one illuminating light beam, a means for initiating a stimulation, a means for detecting the light emerging from the stimulation-specific stains; and means for identifying the spatial position of the regions within the specimen from which light of at least two different wavelengths that are emission wavelengths of the stimulation-specific stains is emerging.

The invention has the advantage that the signal-to-noise problem is substantially no longer present because of the use of two stains, since the probability of random light emission from stimulation-specific stains of different emission wavelengths in the same image region is sufficiently low that is does not influence reliable location of the specimen regions of interest.

Very preferably, detection of the light emerging from the stimulation-specific stains is accomplished in temporal correlation with initiation of the stimulation. For that purpose, the signal generated by the detector is accepted or taken into account by the electronic processing unit only within a time window of defined width after initiation of the stimulation. This action further reduces the probability of false results.

For spectrally sensitive detection, an arrangement of dichroic filters which directs the light emerging from the stimulation-specific stains to different detectors can be used. Preferably, however, a multi-band detector is used. A particularly suitable embodiment of a multi-band detector is known from DE Patent 43 30 347.

The introduction of at least two stimulation-specific stains can encompass the introduction of different fluorochromes, but also the introduction by genetic engineering of fluorescing proteins, in particular GFP (green fluorescent protein). It is also possible to perform the examination on transgenic animals that already possess the corresponding gene sequences. The use of GFP has the advantage that the living specimen is not influenced thereby; for example, the protein-based GFP is not toxic. The stimulation-specific stains can moreover be indicators, in particular calcium indicators.

Advantageously, illumination of the specimen is accomplished with a beam deflection device that guides the illuminating light beam on a defined path over or through the specimen. By identifying the deflection position of the beam deflection device in temporal correlation with detection of the light emerging from the stimulation-specific stains, it is possible to draw conclusions as to the spatial position of the regions of interest. The beam deflection device preferably contains tiltable mirrors, the tilting being brought about e.g. by galvanometers.

In a preferred embodiment, the regions of interest are displayed to the user in a preview image on a display or a monitor.

In a greatly preferred embodiment, the method according to the present invention is carried out with partial use of a scanning microscope, in particular a confocal scanning microscope. The apparatus according to the present invention can contain a scanning microscope, in particular a confocal scanning microscope.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
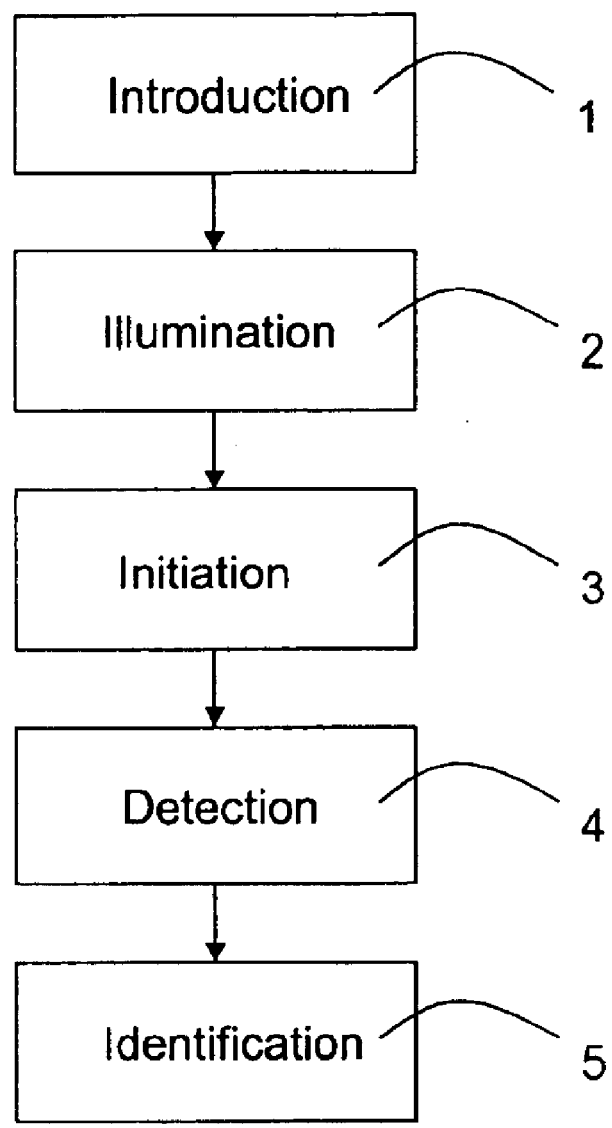
FIG. 1 shows a flow chart of the method according to the present invention.

The flow chart depicted in FIG. 1 illustrates the method according to the present invention. In a first step, introduction 1 into the specimen of at least two stimulation-specific stains that emit light of different wavelengths is performed. These stains can be different fluorochromes or nanocrystals. Introduction can also encompass the introduction by genetic engineering of fluorescent proteins, in particular GFP (green fluorescent protein). The stimulation-specific stains can moreover be indicators, in particular calcium indicators. This is followed by illumination 2 of the specimen or a portion of the specimen with at least one illuminating light beam. The illuminating beam can be widened so that a large area of the specimen is illuminated, or a focused illuminating light beam can be used, the latter being guided with a beam deflection device on a defined path over or through the specimen. In a further step, initiation 3 of a stimulation is accomplished. This can involve, for example, a mechanical manipulation, application of a voltage pulse, or an irradiation with electromagnetic waves. In the next step, detection 4 of the light emerging from the stimulation-specific stains is performed. Said light can be divided in spectrally selective fashion, for example with dichroic beam splitters, so as to be detected by individual detectors. It is also possible to perform the detection with a single detector, preferably a photomultiplier, light that does not possess emission wavelengths of the stimulation-specific stains being filtered out before the detector. Color filters or bandpass filters can be used for this purpose. The use of a multi-band detector is very particularly suitable. The last step comprises identification 5 of the spatial position of the regions within the specimen from which light of at least two different wavelengths that are emission wavelengths of the stimulation-specific stains is emerging. This can be done, for example, indirectly by detecting the deflection position of the beam deflection device in temporal correlation with detection of the light emerging from the stimulation-specific stains.

Figure 2:
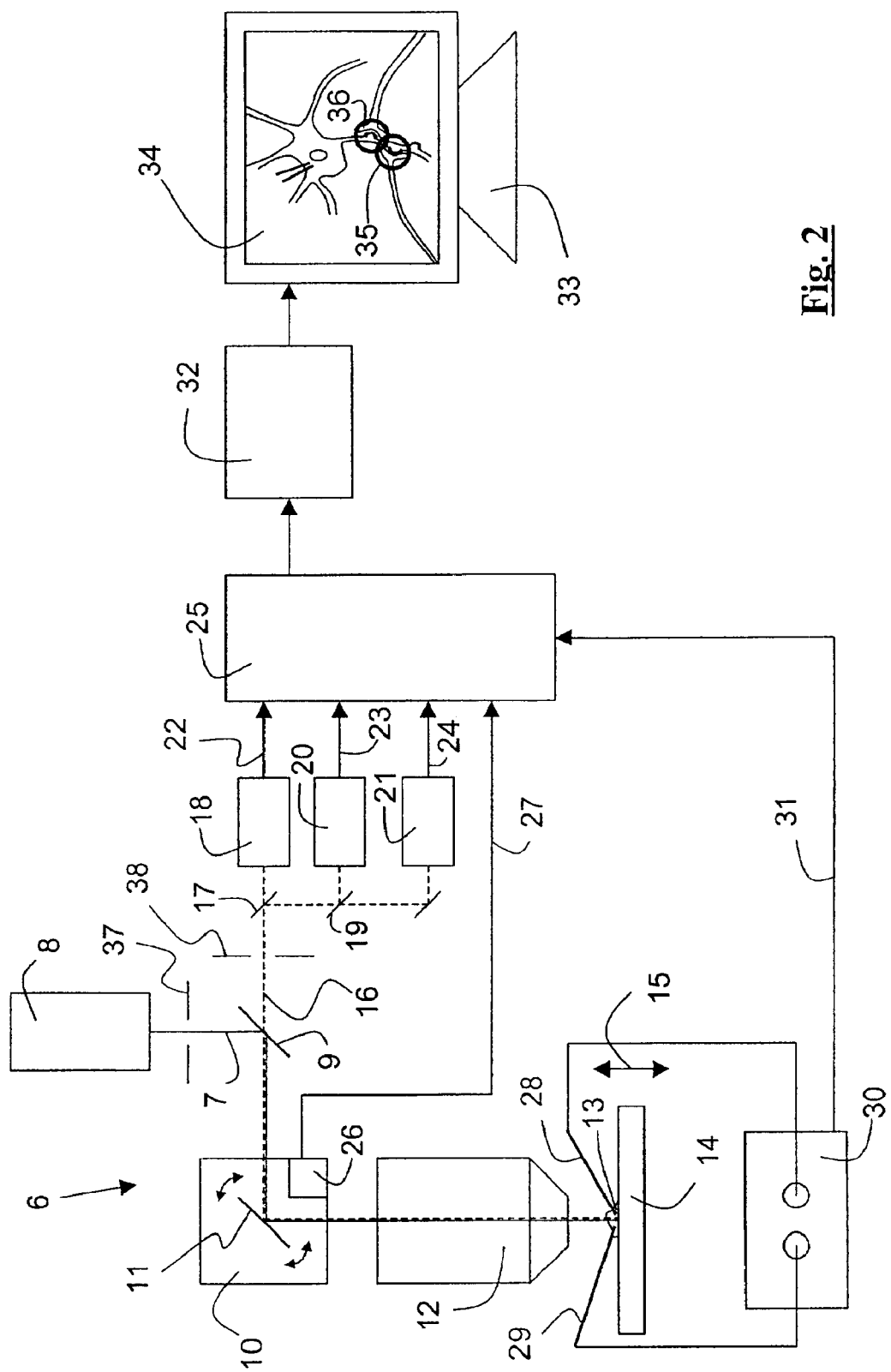
FIG. 2 shows an apparatus according to the present invention with a confocal microscope.

The embodiment depicted in FIG. 2 contains a confocal scanning microscope 6. Illuminating light beam 7 is generated by a laser 8 that is embodied as a multi-line laser, and is reflected by a beam splitter 9 to beam deflection device 10, which contains a gimbal-mounted scanning mirror 11 that guides illuminating light beam 7 through microscope optical system 12 and over or through specimen 13. Specimen 13 is prepared with a first and a second indicator stain, the indicator stains having different emission wavelengths. In the case of non-transparent specimens 13, illuminating light beam 7 is guided over the specimen surface. In the case of biological specimens 13 (preparations) or transparent specimens 13, illuminating light beam 7 can also be guided through specimen 13. This means that different section planes of specimen 13 can be scanned by illuminating light beam 7. Selection of the section planes is accomplished by displacing specimen 13, by means of displaceable specimen stage 14, along directions 15 indicated by the double arrow. Illuminating light beam 7 coming from illumination system 8 is depicted as a solid line. Light 16 emerging from specimen 13 passes through microscope optical system 12 and via beam deflection device 10 to beam splitter 9, passes through the latter and strikes dichroic beam splitter 17, which allows only light of the emission wavelength of the first indicator stain to pass. That light arrives at a first detector 18 that is embodied as a photomultiplier. The rest of the light arrives at a further dichroic beam splitter 19 that reflects only light of the emission wavelength of the second indicator to a second detector 20 which is also embodied as a photomultiplier. The light that passes through the further dichroic beam splitter is conveyed to a third detector 21. Light 16 emerging from specimen 13 is depicted as a dashed line. In detectors 18, 20, 21, electrical detected signals 22, 23, 24 proportional to the power level of the respective light conveyed to them are generated and are forwarded to processing unit 25. Position signals 27 sensed in beam deflection unit 10 with the aid of an inductively or capacitatively operating position sensor 26 are also transferred to processing unit 25. It is self-evident to one skilled in the art that the position of scanning mirror 11 can also be identified by way of the activation signals. In the exemplary embodiment depicted, specimen 13 is equipped with two microelectrodes 28, 29. These are electrically connected to a means for applying an electrical voltage 30 that is embodied as a pulse generator, with which a voltage pulse can be applied to specimen 13 and thus a stimulation can be initiated. Simultaneously with the initiation of a stimulation, an electrical signal 31 is transferred to processing unit 25. After a defined time interval, a time window of defined duration, within which detected signals 22 and 23 are processed, is opened in processing unit 25. Detected signals 22, 23 that arrive outside the time window are very probably unrelated to the initiation of the stimulation and are discarded. Detected signal 24 is used to obtain an overview image. The data are analyzed and processed in the processing unit so that by means of a PC 32 with an attached display 33, an overview image 34 of the scanned section plane of specimen 13, or a three-dimensional view of a volume of specimen 13, in which regions of interest 35, 36 are marked can be displayed. Illumination pinhole 37 and detection pinhole 38 that are usually provided in a confocal scanning microscope are depicted schematically for the sake of completeness. Certain optical elements for guiding and shaping the light beams are, however, omitted in the interest of greater clarity. They are sufficiently familiar to anyone skilled in this art.

Figure 3:
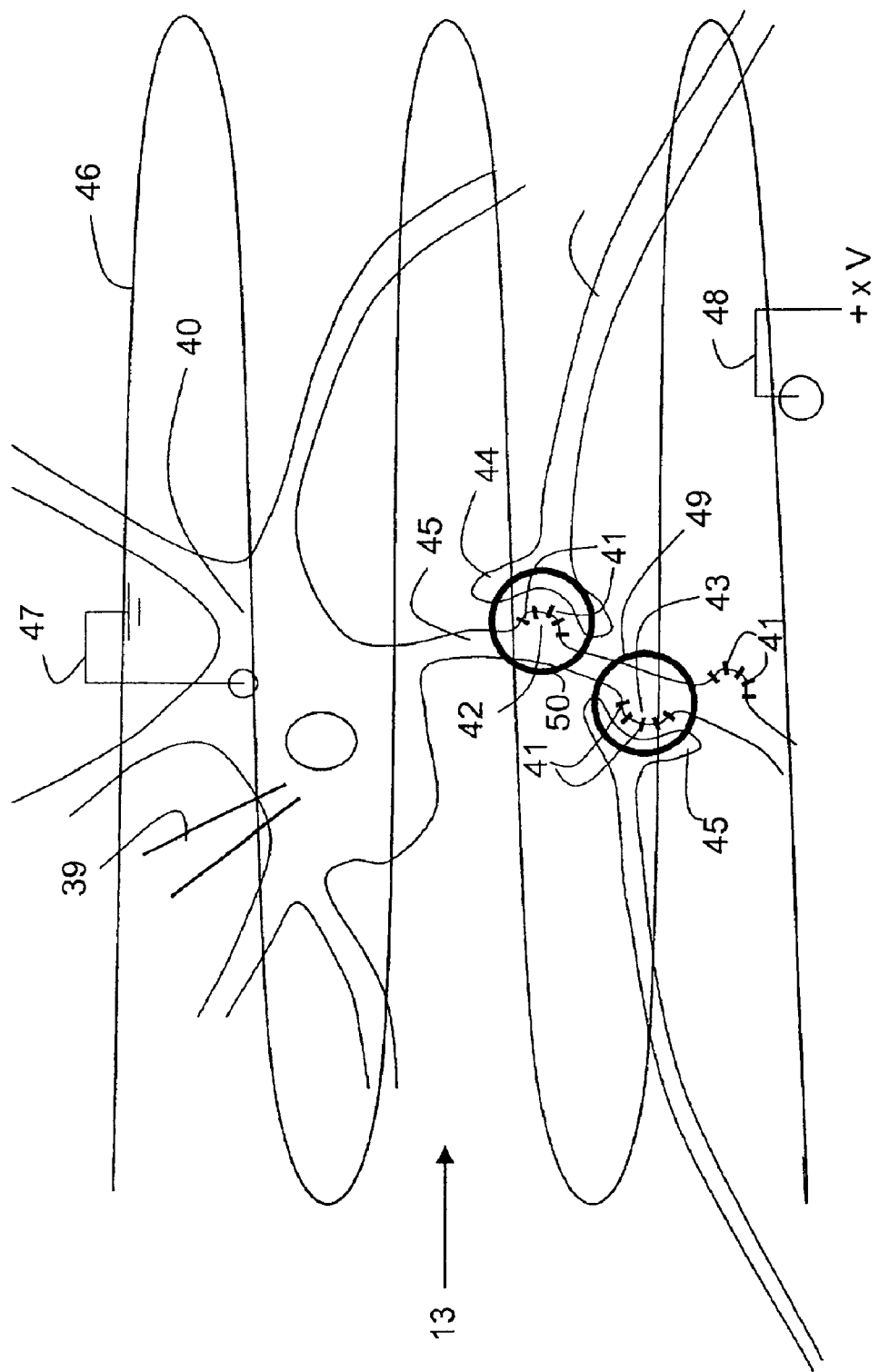
FIG. 3 shows an application of the method according to the present invention in cell biology.

FIG. 3 illustrates an application of the method according to the present invention in cell biology. A micropipette 39 is used to introduce a calcium indicator into nerve cell 40. The calcium indicator fills up the cell and is not depicted. The spines of the nerve cell are labeled with GFP (green fluorescent protein) 41 by genetic-engineering manipulation. Synapses 44, 45 of other nerve cells are coupled to spines 42, 43. The entire specimen section is continuously illuminated, along the depicted scanning track 46, with the focus of an illuminating light beam of wavelengths 488 nm, 514 nm, and 568 nm. A voltage pulse can be applied between the neuron and its environment using micro-patch clamp 47 and microelectrode 48. Since nerve cell 40 is in contact with adjacent nerve cells as described above, the voltage pulse causes calcium to flow in at contact points 49, 50; with rapidly scanning illumination, this can be detected on the basis of the calcium indicators and the GFP (which fluoresces at a different wavelength from the calcium indicator).

The reliability with which contact points 43, 44 can be located is very high, since a contact point 43, 44 can exist only at points at which the GFP and the calcium indicator simultaneously emit light. For increased reliability, detection of the light emerging from the specimen is accomplished in temporal correlation with initiation of the stimulation. The position of contact points 49, 50 is stored and displayed to the user.

The invention was described with reference to a particular embodiment. It is nevertheless self-evident that changes and modifications can be made without thereby leaving the range of protection of the claims recited hereinafter.

What is claimed is:

1. A method for locating specimen regions of interest in a stimulatable microscopic specimen, comprising the following steps:
    introducing into the specimen of at least two stimulation-specific stains that emit light of different wavelengths;
    illuminating at least a portion of the specimen with at least one illuminating light beam;
    initiating a stimulation;
    detecting the light emerging from the stimulation-specific stains; and
    identifying the spatial position of the regions within the portion of the specimen from which light of at least two different wavelengths that are emission wavelengths of the stimulation-specific stains is emerging.

2. The method as defined in claim 1, wherein detecting the light emerging from the stimulation-specific stains is accomplished in temporal correlation with initiation of the stimulation.

3. The method as defined in claim 1, wherein introducing of at least two stimulation-specific stains encompasses the introduction by genetic engineering of fluorescing proteins.

4. The method as defined in claim 3, wherein the fluorescing proteins include GFP.

5. The method as defined in claim 1, wherein the introducing of at least two stimulation-specific stains encompasses the introduction of indicators.

6. The method as defined in claim 5, wherein the indicators include calcium indicators.

7. The method as defined in claim 1, wherein stimulating comprises the application of an electrical voltage.

8. The method as defined in claim 1, wherein illuminating of the specimen comprises, an illuminating light beam guided with a beam deflection device on a defined path over or through the specimen.

9. The method as defined in claim 8, wherein data concerning the deflection position of the beam deflection device are used for identification of the spatial position of the regions within the portion of the specimen.

10. The method as defined in claim 1, wherein the regions within the portion of the specimen are displayed to the user on a means for display.

11. The method as defined in claim 1, wherein the specimen is a biological specimen.

12. The method as defined in claim 11, wherein the regions within the portion of the specimen are contact points between nerve cells.

13. The method as defined in claim 11, wherein the biological specimen includes a nerve cell tissue.

14. The method as defined in claim 1, wherein a scanning microscope is used.

15. The method as defined in claim 14, wherein the scanning microscope includes a confocal scanning microscope.

* * * * *